United States Patent
Bull et al.

(10) Patent No.: US 10,971,273 B2
(45) Date of Patent: Apr. 6, 2021

(54) IDENTIFICATION OF CO-LOCATED ARTIFACTS IN COGNITIVELY ANALYZED CORPORA

(71) Applicant: International Business Machines Corporation, Armonk, NY (US)

(72) Inventors: Brendan Bull, Durham, NC (US); Paul Lewis Felt, Utah County, UT (US); Andrew Hicks, Raleigh, NC (US)

(73) Assignee: International Business Machines Corporation, Armonk, NY (US)

( * ) Notice: Subject to any disclaimer, the term of this patent is extended or adjusted under 35 U.S.C. 154(b) by 336 days.

(21) Appl. No.: 16/041,091

(22) Filed: Jul. 20, 2018

(65) Prior Publication Data

US 2020/0027566 A1 Jan. 23, 2020

(51) Int. Cl.
*G06F 17/28* (2006.01)
*G16H 70/20* (2018.01)
*G06N 20/00* (2019.01)

(52) U.S. Cl.
CPC ............. *G16H 70/20* (2018.01); *G06N 20/00* (2019.01)

(58) Field of Classification Search
CPC ........ G06Q 40/08; G06Q 10/10; G06Q 40/06; G06F 16/24578; G06F 16/3331; G06F 16/34; G06F 16/38; G06F 16/3347; G06F 16/355; G06F 16/93; G06F 16/313; G06F 16/334; G06F 16/335; G06F 16/35; G06F 16/367; G06F 16/9024; G06F 16/9038; G06F 40/169; G06F 40/30; G16H 70/20; G06N 20/00; G06N 3/0454; G06N 3/08
See application file for complete search history.

(56) References Cited

U.S. PATENT DOCUMENTS

| | | | |
|---|---|---|---|
| 2012/0117082 A1* | 5/2012 | Koperda | G06F 16/24578 707/748 |
| 2014/0280088 A1* | 9/2014 | Speer | G06F 16/3347 707/723 |
| 2017/0039198 A1* | 2/2017 | Ramamurthy | G06F 16/93 |
| 2017/0255700 A1* | 9/2017 | Shiffman | G06F 16/951 |
| 2019/0236206 A1* | 8/2019 | Chowdhury | G06F 16/335 |

\* cited by examiner

*Primary Examiner* — Maroun P Kanaan
(74) *Attorney, Agent, or Firm* — Patterson + Sheridan, LLP

(57) ABSTRACT

Techniques for cognitive corpora analysis are provided. Vector representations are generated by processing documents in a corpus using a passage encoder. One or more concepts are identified in the documents by processing the documents with the passage encoder, where the concepts are assigned respective importance scores by the passage encoder. Further, a selection of a document is received, and a sub-corpus of documents is generated by computing a similarity measure between the vector representation of the first document and the vector representation of at least one other document in the corpus. An overall importance score is generated for a first concept, with respect to the generated sub-corpus, by identifying a respective importance score of the first concept in at least two respective documents in the sub-corpus, and aggregating the respective importance scores. Finally, an indication of the generated overall importance score is provided.

19 Claims, 7 Drawing Sheets

200

...
CHEMOPROPHYLAXIS IS RECOMMENDED FOR THE FOLLOWING HIGH RISK GROUPS: NON-IMMUNE VISITORS (TOURISTS) AND PATIENTS WITH SICKLE CELL DISEASE.
...
205

PASSAGE ENCODER
135

150
{...
    -0.0019251,
    0.0150118,
    -0.0040193,
...{

...
proguanil: 0.243042
sickle_cell_disease: 0.138897
antifolate: 0.114932
...
following: 0.000019
or: 0.000018
and: 0.000002
...
155

FIG. 2

IDENTIFICATION OF CO-LOCATED ARTIFACTS IN COGNITIVELY ANALYZED CORPORA

BACKGROUND

The present disclosure relates to corpus analytics, and more specifically, to applying cognitive models to improve identification of co-located concepts in various corpora.

Many data models, such as machine learning models, rely on large corpora of data in order to sufficiently operate. Similarly, a corpus of documents may be interrogated or navigated by users (such as healthcare professionals) to identify co-located concepts, patterns, and the like. Generally, use of a larger corpus enables increased depth of understanding and improved results. However, with increased corpus size, it becomes increasingly difficult to navigate the corpus and identify important collocations, without becoming distracted or mislead by irrelevant or tangential artifacts and correlations. Use of targeted sub-corpora for each particular task would improve efficiency and accuracy, but existing solutions do not provide for practical refinement of larger corpora.

SUMMARY

According to one embodiment of the present disclosure, a method is provided. The method includes generating a plurality of vector representations by processing a plurality of documents in a corpus using a passage encoder, wherein the plurality of vector representations corresponds to respective documents of the plurality of documents. The method further includes identifying one or more concepts in the plurality of documents by processing the plurality of documents with the passage encoder, wherein the one or more concepts are assigned respective importance scores by the passage encoder. Additionally, the method includes receiving a selection of a first document in the plurality of documents, and generating a sub-corpus of documents from the corpus by computing a similarity measure between the vector representation of the first document and the vector representation of at least one other document in the plurality of documents in the corpus. Further, the method includes generating an overall importance score for a first concept of a first plurality of concepts, with respect to the generated sub-corpus, by identifying a respective importance score of the first concept in at least two respective documents in the sub-corpus and aggregating the respective importance scores. Finally, the method includes providing an indication of the generated overall importance score.

According to a second embodiment of the present disclosure, a computer program product is disclosed. The computer program product includes a computer-readable storage medium having computer-readable program code embodied therewith, the computer-readable program code executable by one or more computer processors to perform an operation. The operation includes generating a plurality of vector representations by processing a plurality of documents in a corpus using a passage encoder, wherein the plurality of vector representations corresponds to respective documents of the plurality of documents. The operation further includes identifying one or more concepts in the plurality of documents by processing the plurality of documents with the passage encoder, wherein the one or more concepts are assigned respective importance scores by the passage encoder. Additionally, the operation includes receiving a selection of a first document in the plurality of documents, and generating a sub-corpus of documents from the corpus by computing a similarity measure between the vector representation of the first document and the vector representation of at least one other document in the plurality of documents in the corpus. Further, the operation includes generating an overall importance score for a first concept of a first plurality of concepts, with respect to the generated sub-corpus, by identifying a respective importance score of the first concept in at least two respective documents in the sub-corpus and aggregating the respective importance scores. Finally, the operation includes providing an indication of the generated overall importance score.

According to a third embodiment of the present disclosure, a system is disclosed. The system includes one or more computer processors, and a memory containing a program which when executed by the one or more computer processors performs an operation. The operation includes generating a plurality of vector representations by processing a plurality of documents in a corpus using a passage encoder, wherein the plurality of vector representations corresponds to respective documents of the plurality of documents. The operation further includes identifying one or more concepts in the plurality of documents by processing the plurality of documents with the passage encoder, wherein the one or more concepts are assigned respective importance scores by the passage encoder. Additionally, the operation includes receiving a selection of a first document in the plurality of documents, and generating a sub-corpus of documents from the corpus by computing a similarity measure between the vector representation of the first document and the vector representation of at least one other document in the plurality of documents in the corpus. Further, the operation includes generating an overall importance score for a first concept of a first plurality of concepts, with respect to the generated sub-corpus, by identifying a respective importance score of the first concept in at least two respective documents in the sub-corpus and aggregating the respective importance scores. Finally, the operation includes providing an indication of the generated overall importance score.

BRIEF DESCRIPTION OF THE SEVERAL VIEWS OF THE DRAWINGS

FIG. 2 illustrates a workflow for ingestion of documents or passages in a corpus, according to one embodiment disclosed herein.

DETAILED DESCRIPTION

Embodiments of the present disclosure improve detection of co-occurring cognitive artifacts in cognitively analyzed corpora. In existing solutions, cognitive analytic engines can produce a vast variety of analytic artifacts when being applied over corpus content. Existing services and solutions that provide the capability to discover co-occurring artifacts in the corpus are generally limited to returning results based on semantic group or semantic type(s), which can result in providing artifacts that may be completely unrelated to the original artifact. The unrelated artifacts make it difficult for a corpus navigator to differentiate which co-occurring artifacts will assist rather than hamper corpus navigation.

Embodiments of the present disclosure utilize a machine learning-based passage vector model that is able to create a general purpose representation of a text passage. In embodiments, these representations can be used to cluster documents based on content. This allows for the creation dynamic sub-corpora of a larger corpus that can be used for targeted collocation mining. Further, in embodiments, the passage encoder also provides a weighting of how important a term or concept is to any particular passage. In an embodiment, in addition to restricting the search space based on topical relevance, we can also sort items by potential relevance.

Utilizing embodiments of the present disclosure, navigation and use of diverse corpora are improved. Embodiments of the present disclosure enable dynamic generation and manipulation of increasingly specific sub-corpora. This improves the efficacy of corpus navigation. Further, by generating such targeted sub-corpora, embodiments of the present disclosure can improve the efficiency and accuracy of a large variety of models and systems that rely on corpora. Similarly, ingestion, analysis, and processing of the targeted corpora (as opposed to the entire corpus, or sub-corpora that are not cognitively generated) reduces the computational resources required, as resources are not wasted on concepts and relationships that are irrelevant or tangentially related to the concept(s) that are the focus of the analysis.

Figure 1:
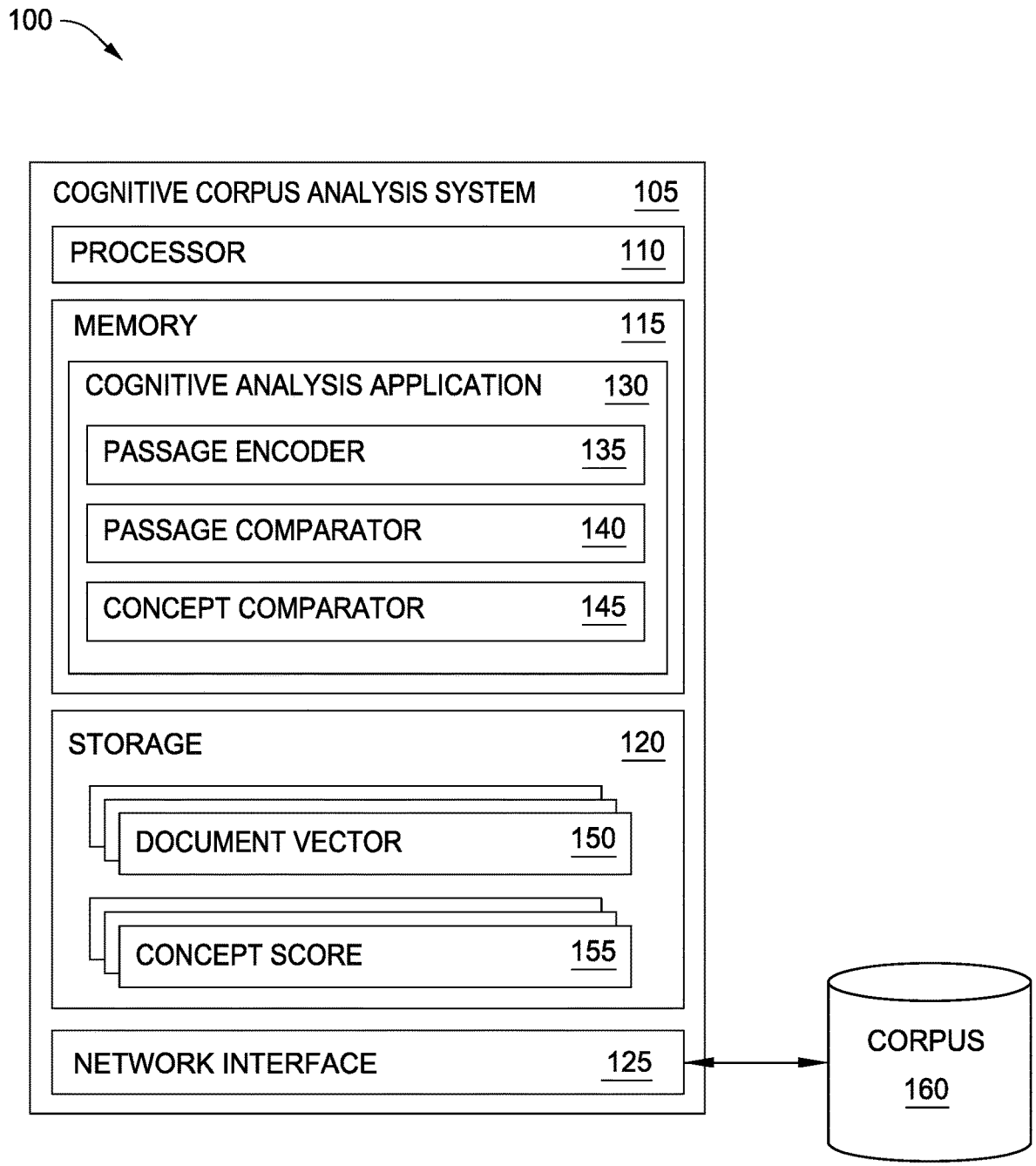
FIG. 1 is a block diagram illustrating a system for cognitive analysis of corpora, according to one embodiment disclosed herein.

FIG. 1 is a block diagram illustrating a system 100 for cognitive analysis of corpora, according to one embodiment disclosed herein. In the illustrated embodiment, the system 100 includes a Cognitive Corpus Analytics System 105, and one or more Corpora 160. As illustrated, the Cognitive Corpus Analytics System 105 includes a Processor 110, a Memory 115, Storage 120, and a Network Interface 125. In the illustrated embodiment, Processor 110 retrieves and executes programming instructions stored in Memory 115 as well as stores and retrieves application data residing in Storage 120. Processor 110 is representative of a single central processing unit (CPU), multiple CPUs, a single CPU having multiple processing cores, and the like. Memory 115 is generally included to be representative of a random access memory. Storage 120 may be a disk drive or flash-based storage device, and may include fixed and/or removable storage devices, such as fixed disk drives, removable memory cards, or optical storage, network attached storage (NAS), or storage area-network (SAN). Through the Network Interface 125, the Cognitive Corpus Analytics System 105 may be communicatively coupled with other devices or repositories, including a Corpus 160. Although a single Corpus 160 is illustrated, in embodiments, any number of Corpora 160 may be utilized.

In the illustrated embodiment, the Storage 120 includes a number of Document Vectors 150 and Concept Scores 155. In an embodiment, each Document Vector 150 includes a multi-dimensional vector representation of a document, passage, or segment of text from a Corpus 160. In some embodiments, documents may also include images, video, audio, and the like, and the Document Vectors 150 may further include vector representations of this multimedia content. Although illustrated as residing in Storage 120, in embodiments, the Document Vectors 150 may reside in one or more remote storage locations. In some embodiments, each Document Vector 150 is stored alongside its corresponding document in the Corpus 160, such as in metadata associated with the respective document. Further, in some embodiments, one or more Corpora 160 may reside locally in the Storage 120.

In an embodiment, the Concept Scores 155 correspond to a generated importance score for each concept in each document in the Corpus 160. Although illustrated as residing in Storage 120, in embodiments, the Concept Scores 155 may reside in one or more remote storage locations. In one embodiment, each Concept Score 155 is related to a particular document in the Corpus 160, and includes scores for multiple concepts found in the single document. In another embodiment, each Concept Score 155 is related to a particular concept found in the Corpus 160, and includes multiple scores for the single concept, each score corresponding to a different document in the Corpus 160. In still another embodiment, each Concept Score 155 corresponds to a single score for a single concept from a single document in the Corpus 160. In some embodiments, each Concept Score 155 is stored in the Corpus 160. For example, in one embodiment, each Concept Score 155 is stored alongside its corresponding document in the Corpus 160, such as in metadata associated with the respective document.

In the illustrated embodiment, the Memory 115 includes a Cognitive Analysis Application 130. As depicted, the Cognitive Analysis Application 130 includes a Passage Encoder 135, a Passage Comparator 140, and a Concept Comparator 145. Although illustrated as discrete components operating as part of the Cognitive Analysis Application 130 for illustrative purposes, in embodiments, each of the Passage Encoder 135, Passage Comparator 140, and Concept Comparator 145 may have their functionality combined or divided into any number of components. Further, the operations discussed herein may be accomplished using hardware, software, or a combination of both hardware and software modules, and may be completed on the Cognitive Corpus Analysis System 105, or divided across one or more other devices.

In an embodiment, the Passage Encoder 135 receives documents from a Corpus 160, generates a vectorized representation of the document, and identifies important concepts, words, and phrases in the document. For example, in an embodiment, the Passage Encoder 135 processes documents to generate a Document Vector 150 and Concept Scores 155 for one or more documents in the Corpus 160 (e.g., for each document). In one embodiment, the Passage Encoder 135 utilizes a machine learning model based on an encoder and decoder architecture. For example, in one embodiment, the Passage Encoder 135 utilizes a recurrent neural network (RNN). Further, in some embodiments, the Passage Encoder 135 additionally utilizes a gated recurrent unit (GRU).

In an embodiment, at training time, the Passage Encoder 135 reads in a sentence, rolls up a vector representation of the sentence, and then uses that representation to make predictions about the surrounding context. In an embodiment, the network is unlikely to perform satisfactorily at the actual prediction task, but this objective puts pressure on the encoder to learn a useful representation of the input text. Further, at runtime, in an embodiment, the decoder side of the network is removed, and the Passage Encoder 135 solely utilizes the encoder. In one embodiment, the attention mechanism used by the Passage Encoder 135 to identify word or concept importance resides on top of the RNN. In one embodiment, in operation, the Passage Encoder 135 returns a vector representation of the input passage and a weighting of important terms. In some embodiments, the Passage Encoder 135 returns importance scores for one or more concepts or words identified in the document. In other embodiments, the Passage Encoder 135 returns scores that exceed a predefined threshold value. In another embodiment, the Passage Encoder 135 returns only the top N words or concepts, where N may be selected by a user or administrator. The vector representation of each document can then be used for classification, clustering, or similarity comparisons. Further, in embodiments, the word importance can be utilized to inform downstream tasks (such as vocabulary expansion).

In the illustrated embodiment, the Passage Comparator 140 is used to generate similarity measures between documents in the Corpus 160 (e.g., between the Document Vectors 150 for each respective document). In one embodiment, the Passage Comparator 140 utilizes cosine similarity to generate similarity measures for each document pair. In some embodiments, the Passage Comparator 140 receives one or more seed documents to be used to identify related documents. For example, in one embodiment, a user may select a document in the Corpus 160 to act as a seed document. In some embodiments, the user may similarly input a document that is not in the Corpus 160 to be ingested and used as a seed document for generating a sub-corpus. In embodiments, the Passage Comparator 140 generates sub-corpora based on seed documents (e.g., based on similarity measures between each vector representation), to identify documents that are similar to the seed document. In one embodiment, the sub-corpora include documents with a similarity measure (as compared to the seed document) that exceeds a predefined threshold (which may be selected by a user). In another embodiment, the sub-corpora include the N documents with the highest similarity measures, where N may be similarly defined by a user.

In one embodiment, the Passage Comparator 140 utilizes a single document or passage as a seed. In other embodiments, the Passage Comparator 140 is configured to utilize multiple documents, should the user desire to do so. For example, in one embodiment, the Document Vectors 150 for the multiple seed documents are aggregated to create an aggregate vector representation, which is then compared with one or more Document Vectors 150 in the Corpus 160. In one embodiment, generating the aggregate vector representation comprises averaging the Document Vectors 150 of each selected seed document. In some embodiments, each seed document may be associated with a weight, and generating the aggregate document vector comprises computing a weighted average of the seed documents. In one embodiment, the weights are specified by a user. In one embodiment, rather than generate aggregate vectors, the Passage Comparator 140 may generate a sub-corpus for each seed document, and the union of the sub-corpora is used as a composite sub-corpus based on the seed documents.

In some embodiments, users can also select documents that exemplify content they wish to exclude from the sub-corpora, in addition to seed documents that exemplify content they wish to include. In one embodiment, such negative documents are incorporated by the Passage Comparator 140 by negating the Document Vector 150 for the selected document prior to aggregating it (e.g., averaging it) with the Document Vector(s) 150 for the other seed document(s). Similarly, in one embodiment, the negated Document Vector 150 is used to generate a sub-corpus, and the composite sub-corpus is represented by the set difference between the sub-corpora (e.g., the composite sub-corpus includes all documents in any of the sub-corpora generated using a positive seed document, and excluding all documents found in the sub-corpora corresponding to the negative document(s)).

Thus, in embodiments, the Passage Comparator 140 utilizes one or more identified documents to generate sub-corpora of documents from a larger corpus that are closely related to the identified documents. In some embodiments, this process may be iteratively refined to generate progressively more targeted sub-corpora. In an embodiment, a user may select a first article, passage, or document to generate a corresponding sub-corpus. The user may then select a document (either in the generated sub-corpus, or outside of the sub-corpus) to further refine the sub-corpus. For example, the user may select a document relating to a topic such as complications with diabetes in order to generate a sub-corpus relevant to this topic. The user may then identify one or more documents in this sub-corpus that are particularly relevant to the specific domain the user is interested in, and utilize these documents as further seed documents to narrow the sub-corpus. Similarly, the user may identify one or more documents that are unrelated, tangential, or otherwise not desired, and use these documents as negative examples for further refinement of the sub-corpus. In this way, sub-corpora can be iteratively generated and dynamically refined.

In the illustrated embodiment, the Concept Comparator 145 utilizes selected concepts to further refine or navigate the sub-corpora. That is, in embodiments, both concepts and documents can both be used to divide the corpora into more targeted sub-corpora. As discussed above, in an embodiment, the Passage Encoder 135 generates importance scores for each concept in each document in the Corpus 160. In one embodiment, a user may utilize these concepts to refine the Corpus 160. For example, in one embodiment, a concept may be selected, and the Concept Comparator 145 may identify documents in the Corpus 160 (or in a sub-corpus) where the selected concept has an importance score above a predefined threshold. This sub-corpus can similarly be further refined based on additional seed documents or additional concepts, in order to cognitively identify co-located concepts of particular relevance or importance, as discussed in more detail below.

FIG. 2 illustrates a workflow 200 for ingestion of documents or passages in a corpus, according to one embodiment disclosed herein. The illustrated embodiment includes a Document 205 relating to chemoprophylaxis for treatment or prevention of malaria. As illustrated by the ellipses above and below the text in the Document 205, the actual length of the input document can vary. Further, although referred to as a "document," in embodiments, the input may be any length of text, including a portion or fragment of a document, a passage, a sentence, a paragraph, and the like. As illustrated, the Document 205 is provided to the Passage Encoder 135, which generates a Document Vector 150 and Concept Scores 155. In the illustrated embodiment, the Document Vector 150 is a multidimensional vector representation of the input Document 205. Although three dimensions are enumerated in the illustrated Document Vector 150, in embodiments, the Document Vector 150 may be any length (as indicated by the ellipses). In some embodiments, the number of dimensions of the encoded Document Vectors 150 is defined by a user or administrator.

As illustrated, the Passage Encoder 135 also generated Concept Scores 155 for the input Document 205. For example, "proguanil" has a score of 0.243042, while "or" has a score of 0.000018. In the illustrated embodiment, each concept may be a single word (such as "proguanil") or a phrase including multiple words (such as "sickle cell disease"). As illustrated, in some embodiments, stop words and other common phrases do receive some voltage (e.g., do have some importance score), but this score is very low because the Passage Encoder 135 understands that such words are unlikely to be predictive of topicality. As discussed above, in some embodiments, only the top N concepts (as determined by the generated importance scores), or concepts with an importance score exceeding a predefined threshold, are returned and stored for the Document 205. In some embodiments, an "expected" importance is determined, and concepts may be selected based on this "expected" importance. In one embodiment, the expected importance of each word is computed based on the total number of words (or the total number of unique words) in the input Document 205. For example, if an input document includes 100 words (or 100 unique words), the expected importance of each (unique) word may be one divided by one hundred, or 0.01. In one embodiment, importance scores exceeding this value are retained for future use, because the corresponding words are more important than the "expected" importance of each average word.

In one embodiment, the Passage Encoder 135 is trained to identify important words or concepts based on their relative frequency in the particular Document 205, as well as their relative scarcity with respect to the overall Corpus 160. For example, if a word is found frequently in a particular Document 205, but is also found frequently throughout the Corpus 160, it is unlikely to be a particularly important word for the Document 205 (that is, it is not likely to be a uniquely important word to the particular Document 205, because it is common in the Corpus 160). Similarly, if a word or concept is not found frequently in a particular Document 205, it is also not likely to be relatively important. Conversely, in an embodiment, if a word is found relatively frequently in the Document 205 (as compared to other documents), and is found relatively infrequently in the overall Corpus 160, it is likely to be a relatively more important word for the particular Document 205. In an embodiment, importance scores are generated for each concept based on this relative frequency and rarity.

In the illustrated embodiment, a single Passage Encoder 135 is depicted. In some embodiments, the Cognitive Analysis Application 130 may utilize multiple Passage Encoders 135. For example, in one embodiment, the Passage Encoders 135 may be trained to be more sensitive to particular relationships or concepts. In such an embodiment, in addition to providing one or more seed documents, a user may also select a Passage Encoder 135 to be used when generating the sub-corpora, based on the desired area of interest.

Figure 3:
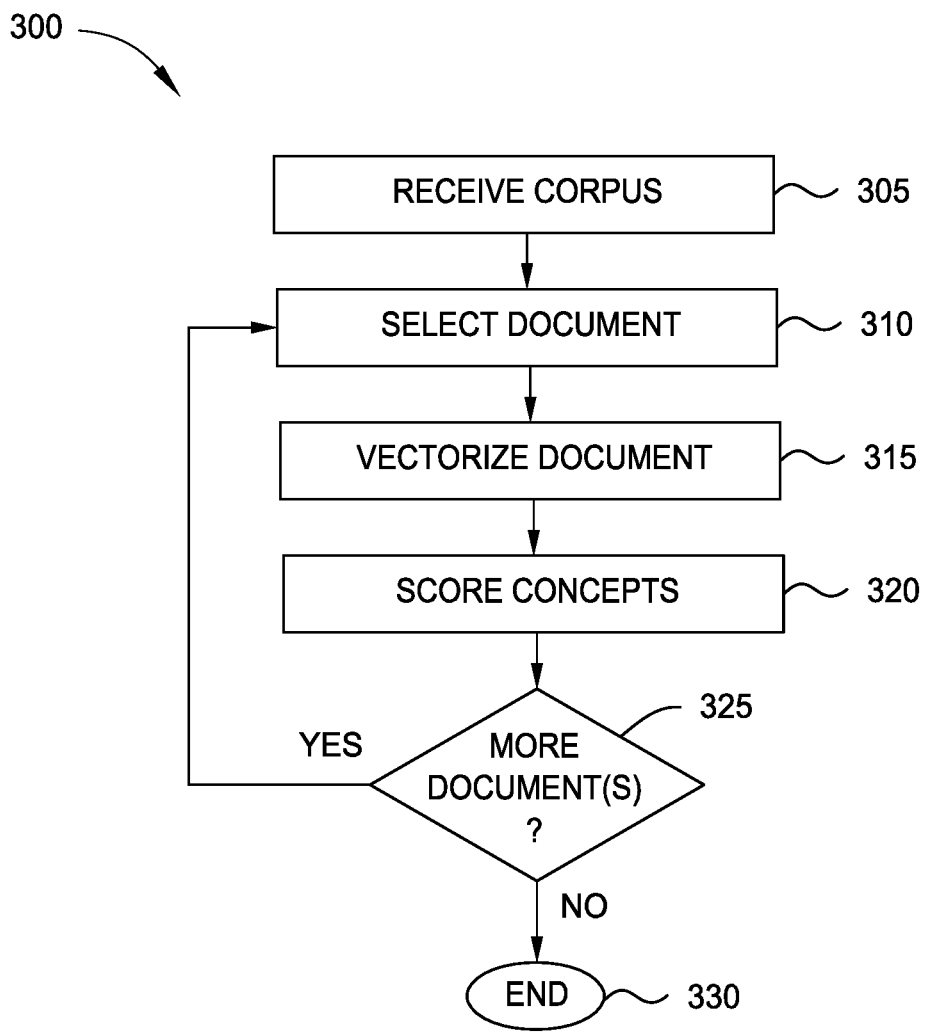
FIG. 3 is a flow diagram illustrating a method for cognitive data ingestion, according to one embodiment disclosed herein.

FIG. 3 is a flow diagram illustrating a method 300 for cognitive data ingestion, according to one embodiment disclosed herein. The method 300 begins at block 305, where the Cognitive Analysis Application 130 receives a corpus of documents to be ingested. In embodiments, this may include receiving the corpus itself, as well as receiving an indication of or a link to the desired corpus. At block 310 the Cognitive Analysis Application 130 selects a first document in the indicated corpus. The method 300 then proceeds to block 315, where the Cognitive Analysis Application 130 vectorizes the selected document (such as via a Passage Encoder 135). In some embodiments, the Cognitive Analysis Application 130 may generate multiple vector representations for each document (such as by using multiple Passage Encoders 135). The method 300 then proceeds to block 320, where the Cognitive Analysis Application 130 generates importance scores for each concept in the selected document. Similarly, in some embodiments, the Cognitive Analysis Application 130 utilizes multiple Passage Encoders 135 to generate multiple sets of importance scores for the document. At block 325, the Cognitive Analysis Application 130 determines whether there are additional documents remaining in the corpus. If so, the method 300 returns to block 310. Otherwise, the method 300 terminates at block 330.

In the illustrated embodiment, the method 300 is used to ingest corpora for future processing. In one embodiment, the method 300 is used during an initialization or training phase of the Cognitive Analysis Application 130, in order to generate Document Vectors 150 and Concept Scores 155 for any number of documents and any number of corpora. In this way, when a user subsequently accesses the Cognitive Analysis Application 130 to generate dynamic sub-corpora, processing time is reduced. For example, in an embodiment, ingesting an entire corpus may require a significant amount of time and resources, as compared to ingesting a single document or comparing documents and concepts. In embodiments, the subsequent run-time phase (when users submit individual documents and concepts, and generate dynamic sub-corpora), can generally be executed in near-real time, which allows the Cognitive Analysis Application 130 to remain highly interactive.

Figure 4:
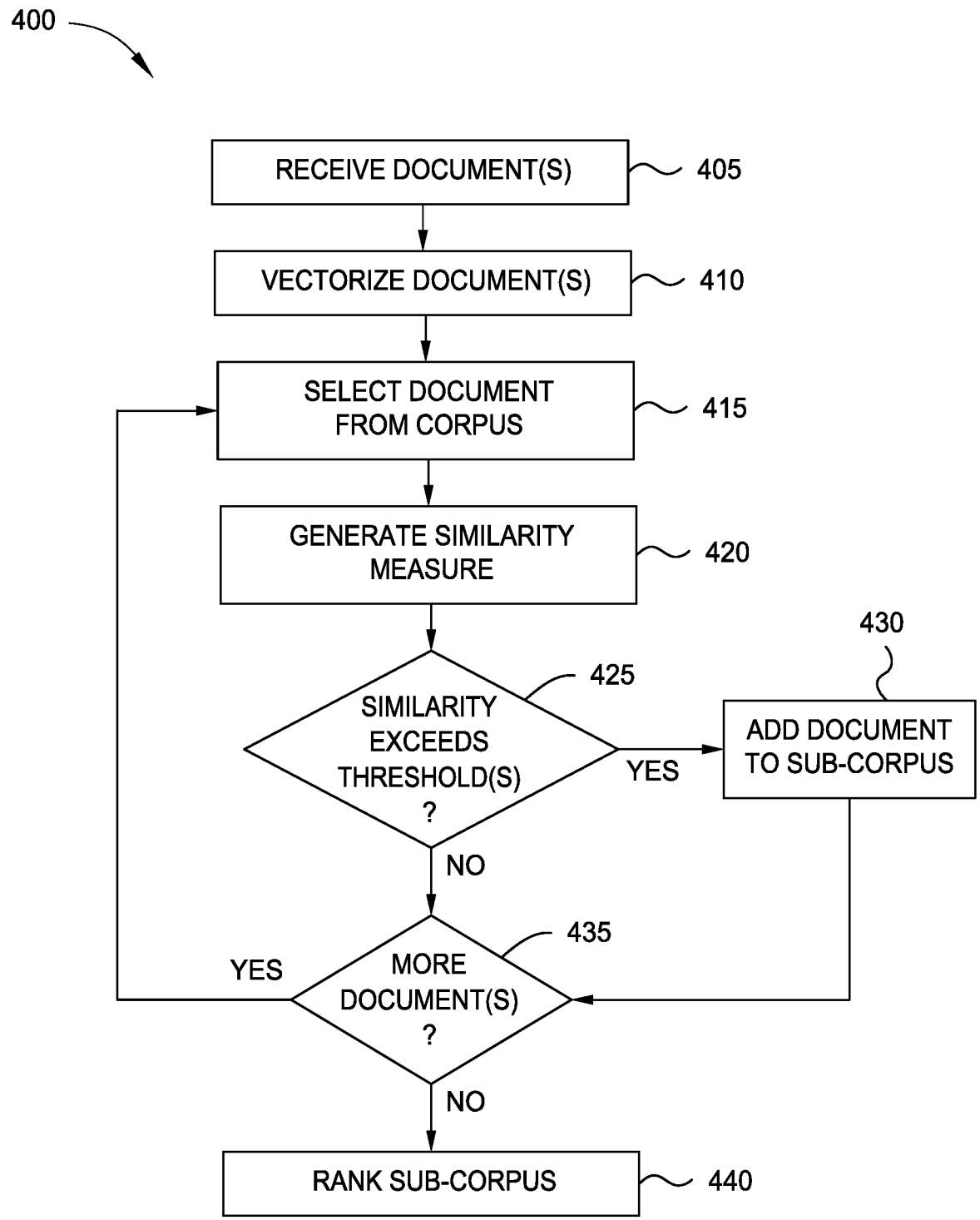
FIG. 4 is a flow diagram illustrating a method for generation of dynamic sub-corpora based on seed documents, according to one embodiment disclosed herein.

FIG. 4 is a flow diagram illustrating a method 400 for generation of dynamic sub-corpora based on seed documents, according to one embodiment disclosed herein. In the illustrated embodiment, the method 400 begins at block 405, where the Cognitive Analysis Application 130 receives one or more documents to be used to generate a sub-corpus. In one embodiment, block 405 corresponds to a user uploading or otherwise selecting one or more documents. In some embodiments, each indicated document may be flagged as a positive or negative example, indicating whether similar or dissimilar documents are desired. In some embodiments, the Cognitive Analysis Application 130 also receives a selection of one or more corpora to be searched. Additionally, in embodiments, the corpus to be searched may be an entire corpus, multiple corpora, or one or more dynamic sub-corpora that the user has generated. Similarly, in one embodiment, the Cognitive Analysis Application 130 further receives an indication of one or more Passage Encoders 135 to utilize when generating the sub-corpora.

The method 400 then proceeds to block 410, where the Cognitive Analysis Application 130 vectorizes the indicated document(s) (e.g., the Cognitive Analysis Application 130 generates one or more Document Vectors 205). As discussed above, in some embodiments, the Cognitive Analysis Application 130 may also aggregate the Document Vectors 205 if multiple seed documents are provided. Further, in an embodiment, if the selected document(s) have already been processed (e.g., because they are already in one or more of the Corpora 160 used by the Cognitive Analysis Application 130), the Cognitive Analysis Application 130 may retrieve the corresponding Document Vectors 150 rather than generate them again.

At block 415, the Cognitive Analysis Application 130 selects a first document from the indicated corpus (or sub-corpus). The method 400 then proceeds to block 420, where the Cognitive Analysis Application 130 generates a similarity measure based on comparing the Document Vector 150 for the selected document and the generated or identified vector representation for the input document(s). For example, in one embodiment, the Cognitive Analysis Application 130 computes the cosine similarity between the vectors. The method 400 then proceeds to block 425, where the Cognitive Analysis Application 130 determines whether the similarity measure exceeds a predefined threshold. In some embodiments, this threshold is defined by the user or by an administrator. If the computed similarity measure does not exceed the threshold, the method 400 proceeds to block 435, discussed in more detail below.

If, however, the Cognitive Analysis Application 130 determines that the selected document is sufficiently similar (as determined based on the comparison between the similarity measure and the predefined threshold), the method 400 proceeds to block 430, where the Cognitive Analysis Application 130 adds the selected document to the sub-corpus that is being generated. The method then continues to block 435. At block 435, the Cognitive Analysis Application 130 determines whether there are additional documents in the corpus that have yet to be processed. If so, the method 400 returns to block 415 to select the next document. Otherwise, the method 400 proceeds to block 440. In the illustrated embodiment, documents are included and excluded from the sub-corpus based on whether the corresponding similarity measure exceeds a predefined threshold. In some embodiments, however, the documents may be ranked (based on the similarity measures), and the N highest-scored documents may be selected for inclusion in the sub-corpus.

As illustrated, at block 440, the Cognitive Analysis Application 130 optionally ranks the generated sub-corpus. In some embodiments, the sub-corpus is returned to the requesting entity without further processing. In the illustrated embodiment, however, the documents in the sub-corpus are ranked and/or sorted based on their individual similarity scores. In an embodiment, this generated sub-corpus may be used as fresh input to the method 400 (along with one or more additional seed documents) to generate further dynamic sub-corpora. For example, a user may review one or more documents in the generated sub-corpus, and select one or more to be used as positive or negative seeds to further refine the sub-corpus. Thus, by utilizing the method 400, the Cognitive Analysis Application 130 can generate any number of iterative and dynamic sub-corpora, which allows for rapid and efficient sub-division of large corpora into manageable and relevant subsets. In embodiments, the user may select whether to search within the generated sub-corpus, or to initiate a new search through the entire corpus based on the additional seed document(s).

Figure 5:
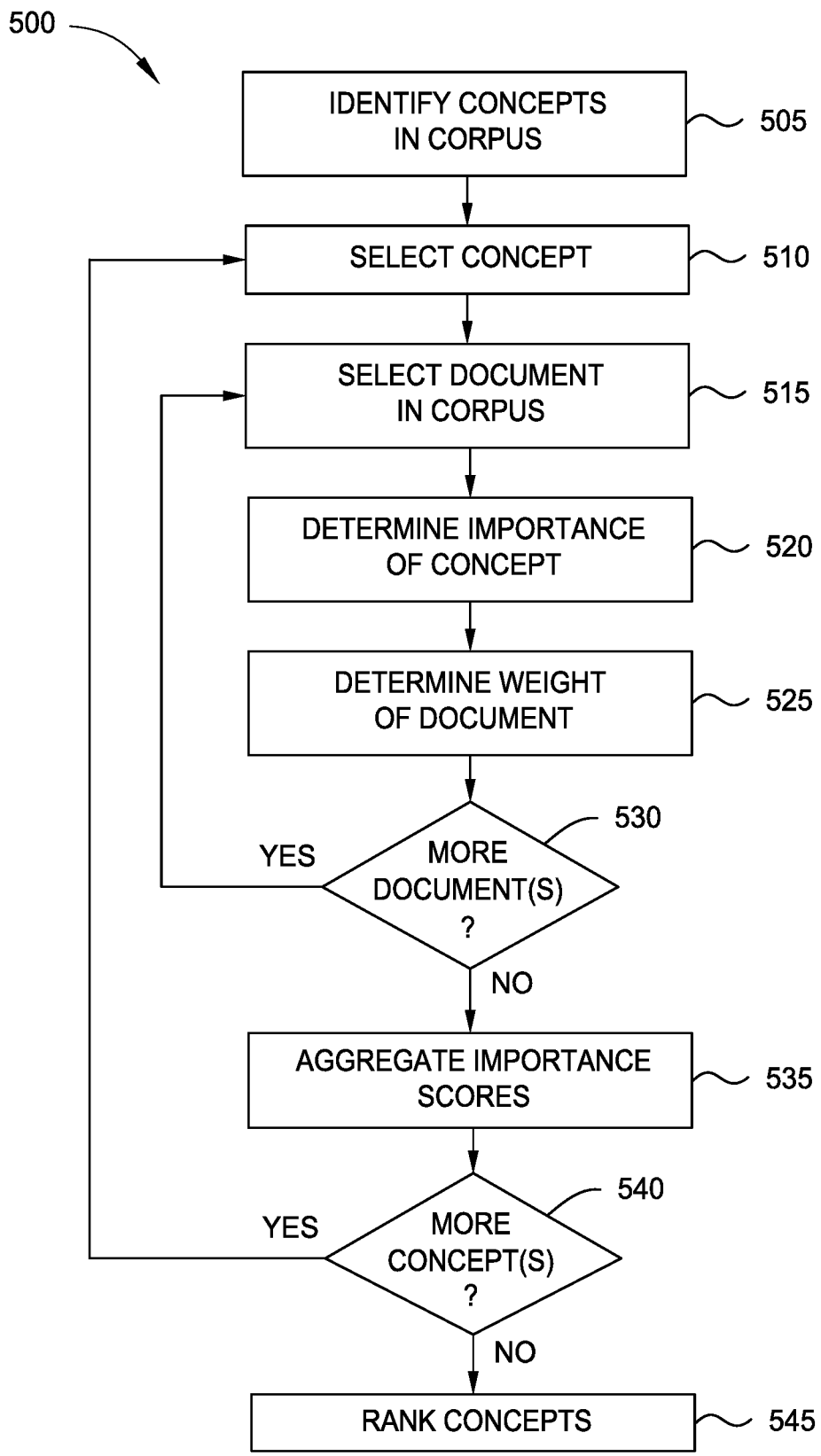
FIG. 5 is a flow diagram illustrating a method for cognitive identification of relevant collocations in dynamic sub-corpora, according to one embodiment disclosed herein.

FIG. 5 is a flow diagram illustrating a method 500 for cognitive identification of relevant collocations in dynamic sub-corpora, according to one embodiment disclosed herein. The method 500 begins at block 505, where the Cognitive Analysis Application 130 identifies concepts in a corpus. In one embodiment, the relevant corpus is selected or indicated by a user. For example, in one embodiment, the corpus corresponds to a sub-corpus generated based on a seed document, as discussed above in reference to FIG. 4, or generated based on one or more selected concepts, as discussed below in reference to FIG. 6. The method 500 then proceeds to block 510, where the Cognitive Analysis Application 130 selects a first identified concept in the corpus (or sub-corpus). At block 515, the Cognitive Analysis Application 130 further selects a first document in the corpus. The method 500 continues to block 520, where the Cognitive Analysis Application 130 determines the importance of the selected concept with respect to the selected document. For example, in an embodiment, the Cognitive Analysis Application 130 determines the importance score that was generated for the selected concept when the selected document was ingested. In one embodiment, if an importance score is not found for the selected concept in the selected document (or if the importance score is below a predefined threshold), the Cognitive Analysis Application 130 assigns a score of zero.

The method 500 then proceeds to block 525, where the Cognitive Analysis Application 130 optionally determines the weight of the selected document. In some embodiments, the documents in the corpus or sub-corpus are weighted equally when identifying important collocations. In other embodiments, the important co-located concepts are scaled towards documents that are most similar to the seed document(s). In such an embodiment, the weight of any particular document may be based at least in part on the proximity of the document to the seed document(s) used to create the sub-corpus. For example, in one embodiment, the weight of the selected document may be based on the computed similarity measure between the selected document and the seed document(s). In such an embodiment, documents that are particularly relevant or similar to the seed document are thereby provided increased weight, in order to scale the identification of other important terms towards these documents.

As illustrated, the method 500 then continues to block 530, where the Cognitive Analysis Application 130 determines whether there are additional documents in the corpus (or sub-corpus) that are yet to be processed with respect to the selected concept. If at least one additional document remains, the method 500 returns to block 515 to select the next document. Otherwise, the method continues to block 535, where the Cognitive Analysis Application 130 aggregates the importance scores corresponding to one or more documents in the corpus, with respect to the selected concept. In one embodiment, aggregating the importance scores comprises computing the sum of the scores. In another embodiment, aggregating the importance sores comprises determining the average, mean, or median importance score. In some embodiments, as discussed above, the importance scores are weighted based on the determined weight of their respective documents. In one embodiment, aggregating the importance scores includes determining the frequency of the concept in the corpus. For example, in such an embodiment, the Cognitive Analysis Application 130 may determine the percentage of documents in the corpus (or sub-corpus) that include the concept.

Once the aggregate or overall importance score for the selected concept has been determined, the method 500 continues to block 540, where the Cognitive Analysis Application 130 determines whether there are additional concepts in the corpus or sub-corpus that are yet to be considered. If so, the method 500 returns to block 510 to select the next concept for processing. Otherwise, the method 500 continues to block 545. As illustrated, at block 545, the Cognitive Analysis Application 130 optionally ranks the concepts in the corpus, based on their respective overall or aggregate importance scores. In some embodiments, in addition to or instead of ranking and sorting the concepts, the Cognitive Analysis Application 130 returns an indication as to a subset of the concepts with associated overall importance scores that exceed a predefined threshold.

Thus, by utilizing the method 500, the Cognitive Analysis Application 130 can score and rank concepts found in the domain (e.g., in the sub-corpus) based on their relative importance to the overall domain, rather than to any individual document. This may enable the user to select one or more concepts for inclusion or exclusion from further search, and allow the user to better understand and refine the sub-corpora. Embodiments of the present disclosure thereby enable a deeper understanding of the domain, which can improve the efficacy and accuracy of subsequent decision-making. Notably, embodiments of the present disclosure enable the identification of co-located concepts and relative document relevance based on complex patterns and relationships within and between documents which are often imperceptible to an ordinary observer. In embodiments, this may facilitate the discovery of additional relationships that are otherwise unknown and undetectable, which further improves understanding of whatever technology, field, or domain is being analyzed.

Figure 6:
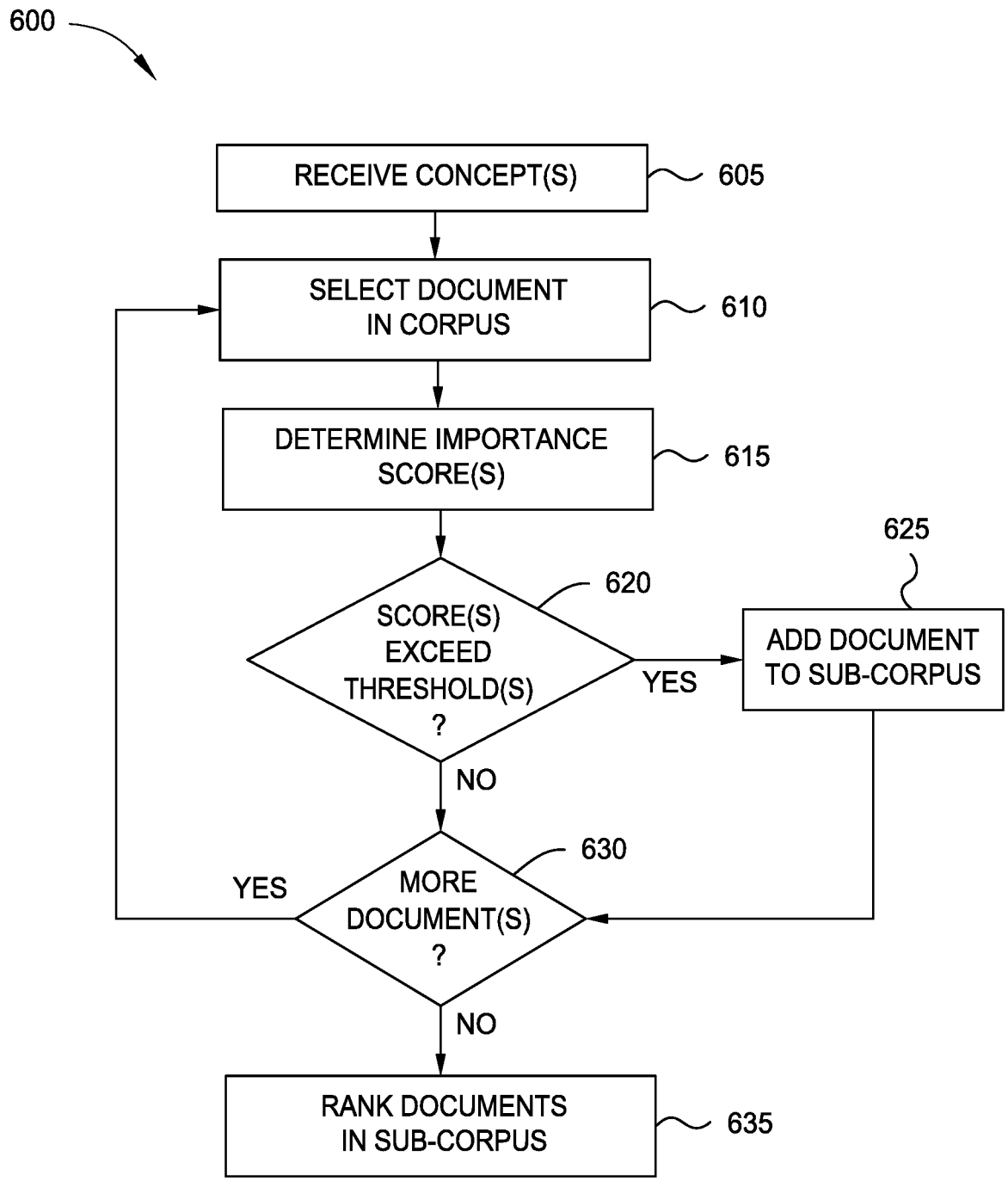
FIG. 6 is a flow diagram illustrating a method for iterative generation of sub-corpora based on identified concepts, according to one embodiment disclosed herein.

FIG. 6 is a flow diagram illustrating a method 600 for iterative generation of sub-corpora based on identified concepts, according to one embodiment disclosed herein. In the illustrated embodiment, the method 600 begins at block 605, where the Cognitive Analysis Application 130 receives one or more concepts. In one embodiment, these concept(s) are identified, selected or otherwise indicated by a user. In some embodiments, the Cognitive Analysis Application 130 also receives an indication as to the corpus or sub-corpus to be processed. For example, in one embodiment, a user may generate a sub-corpus based on the method 400, identify important co-located concepts based on the method 500, select one or more of these identified concepts, and use the selected concept(s) to further refine the dynamic sub-corpus using the method 600.

At block 610, the Cognitive Analysis Application 130 selects a first document in the indicated corpus or sub-corpus. At block 615, the Cognitive Analysis Application 130 determines the importance score(s) associated with the identified concept(s) with respect to the selected document. The method 600 then proceeds to block 620, where the Cognitive Analysis Application 130 determines whether the importance scores of the indicated concept(s), with respect to the selected document, exceed one or more predefined thresholds. In one embodiment, each received concept is compared to a single predefined threshold. In other embodiments, the importance score of each received concept (with respect to the selected document) may be compared distinct thresholds. In one embodiment, the threshold(s) are specified by the user.

Further, in one embodiment, comparing the determined importance score(s) to the threshold(s) comprises determining whether all of the threshold(s) is met or exceeded. In other embodiments, block 620 includes determining whether any of the thresholds are met or exceeded, even if some are not. In some embodiments, block 620 comprises determining whether a predefined number or percentage of the thresholds are met or exceeded. In one embodiment, the particular methodology to determine whether the score(s) exceed the threshold(s) is determined based on user input. Regardless of the particular implementation, in the illustrated embodiment, if the requisite threshold(s) are exceeded, the method 600 proceeds to block 625, where the selected document is added to the newly generated sub-corpus. As discussed above, in embodiments, the corpus utilized in block 610 may already be a dynamic sub-corpus. In such an embodiment, the sub-corpus created in block 625 is a subset or sub-corpus of the already generated sub-corpus. The method 600 then proceeds to block 630.

Additionally, if the Cognitive Analysis Application 130 determines, at block 620, that the criteria is not satisfied, the method proceeds to block 630. In the illustrated embodiment, documents are added or excluded from the sub-corpus based on whether the importance score(s) of the identified concept(s) exceed one or more predefined thresholds. In some embodiments, the Cognitive Analysis Application 130 generates a sub-corpus that includes a predefined number of documents, N, which may be selected based on the relative importance scores. For example, in such an embodiment, the Cognitive Analysis Application 130 may determine the importance scores of each identified concept with respect to each of one or more documents in the corpus, and include the top N documents in the sub-corpus.

At block 630, the Cognitive Analysis Application 130 determines whether there are additional documents in the corpus to be processed. If so, the method 600 returns to block 610 to select the next document. If no documents remain in the corpus, the method 600 proceeds to block 635, where the Cognitive Analysis Application 130 optionally ranks the documents in the sub-corpus. In this way, utilizing the method 600, the Cognitive Analysis Application 130 can further refine the dynamic sub-corpora based on particular concept(s) that the user is most interested in. In an embodiment, this newly generated sub-corpus may be utilized with other embodiments disclosed herein, such as methods 400 or 500, to further identify other documents and co-located concepts that are important to the new sub-corpus. Thus, embodiments, of the present disclosure enable powerful iterative generation of dynamic corpora, which empowers significantly improved depth of understanding of the domain, concepts, and corpus.

Figure 7:
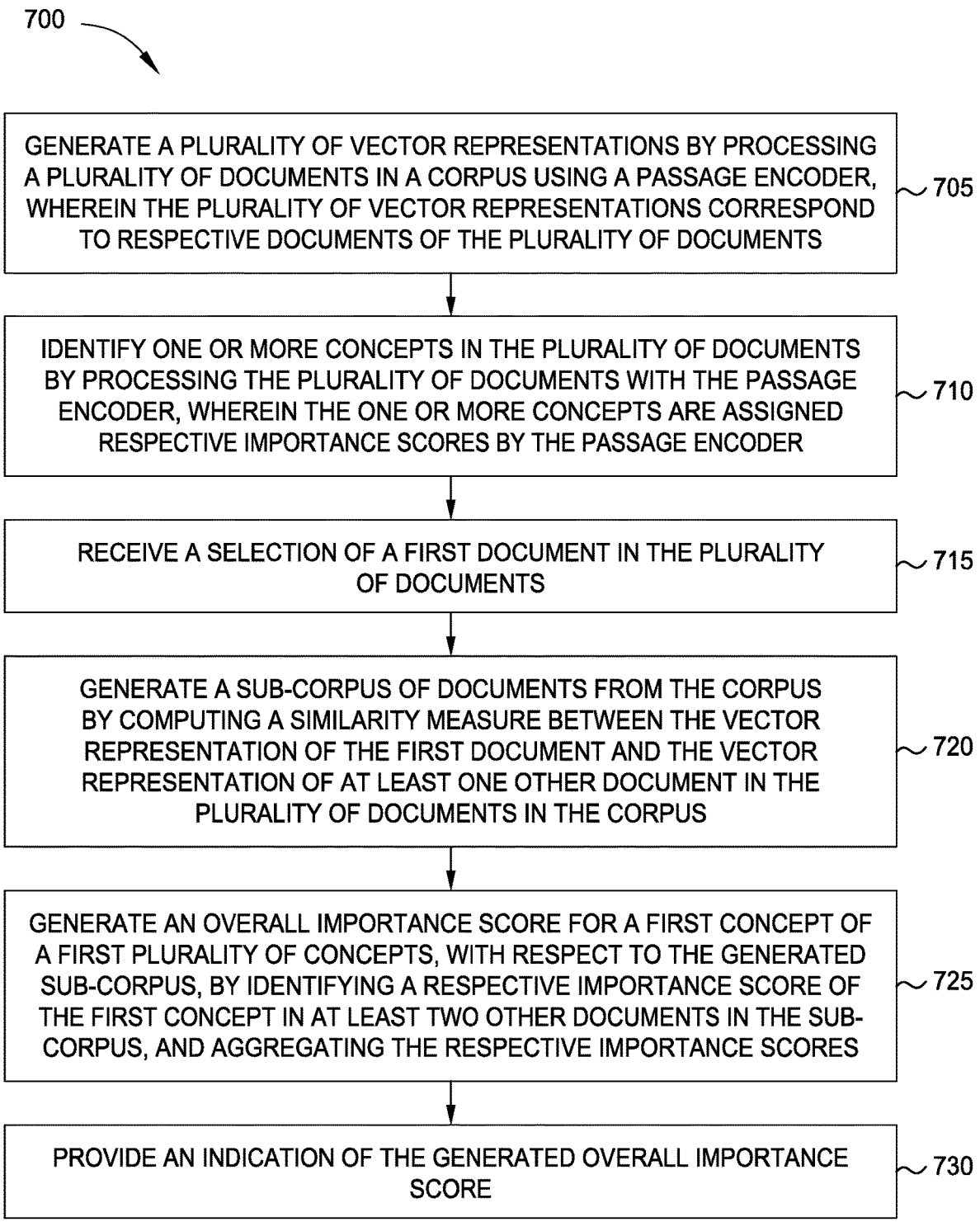
FIG. 7 is a flow diagram illustrating a method for cognitive corpora analysis, according to one embodiment disclosed herein.

FIG. 7 is a flow diagram illustrating a method 700 for cognitive corpora analysis, according to one embodiment disclosed herein. The method 700 begins at block 705, where the Cognitive Analysis Application 130 generates a plurality of vector representations by processing a plurality of documents in a corpus using a passage encoder, wherein the plurality of vector representations correspond to respective documents of the plurality of documents. At block 710, the Cognitive Analysis Application 130 identifies one or more concepts in the plurality of documents by processing the plurality of documents with the passage encoder, wherein the one or more concepts are assigned respective importance scores by the passage encoder. The method 700 then proceeds to block 715, where the Cognitive Analysis Application 130 receives a selection of a first document in the plurality of documents. At block 720, the Cognitive Analysis Application 130 generates a sub-corpus of documents from the corpus by computing a similarity measure between the vector representation of the first document and the vector representation of at least one other document in the plurality of documents in the corpus. The then method 700 continues to block 725, where the Cognitive Analysis Application 130 generates an overall importance score for a first concept of a first plurality of concepts, with respect to the generated sub-corpus, by identifying a respective importance score of the first concept in at least two respective documents in the sub-corpus and aggregating the respective importance scores. Finally, at block 730, the Cognitive Analysis Application 130 provides an indication of the generated overall importance score.

In one embodiment, providing the indication of the overall importance score includes providing the score itself to a user. In one embodiment, the indication of the overall importance score is an indication as to whether the concept is important or not to the sub-corpus. For example, in an embodiment, a predefined threshold is used to determine whether or not the concept is "important." Further, in some embodiments, the concepts may be color-coded or be displayed differently (e.g., in differing font sizes or in different locations on a display) based on their respective importance. In embodiments, providing the indication of the overall importance score may therefore comprise any number of indications, including audio and visual indications, of the importance of the concept.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the preceding, reference is made to embodiments presented in this disclosure. However, the scope of the present disclosure is not limited to specific described embodiments. Instead, any combination of the preceding features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the preceding aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present embodiments may take the form of an entirely hardware embodiment, an entirely software embodiment (including firmware, resident software, microcode, etc.) or an embodiment combining software and hardware aspects that may all generally be referred to herein as a "circuit," "module" or "system."

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the invention may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present invention, a user may access applications (e.g., the Cognitive Analysis Application 130) or related data available in the cloud. For example, the Cognitive Analysis Application 130 could execute on a computing system in the cloud and provide iterative refinement of dynamic corpora. In such a case, the Cognitive Analysis Application 130 could analyze various documents and store document vectors, concept scores, and dynamic sub-corpora at a storage location in the cloud. Doing so allows a user to access this information from any computing system attached to a network connected to the cloud (e.g., the Internet).

While the foregoing is directed to embodiments of the present invention, other and further embodiments of the invention may be devised without departing from the basic scope thereof, and the scope thereof is determined by the claims that follow.

What is claimed is:

1. A method comprising:
   generating a plurality of vector representations by processing a plurality of documents in a corpus using a passage encoder, wherein the plurality of vector representations correspond to respective documents of the plurality of documents;
   identifying one or more concepts in the plurality of documents by processing the plurality of documents with the passage encoder, wherein the one or more concepts are assigned respective importance scores by the passage encoder;
   receiving a selection of a first target document and a second target document from the plurality of documents to be used to generate a sub-corpus of documents from the corpus;
   generating an aggregate vector representation for the first and second target documents by averaging vector representations for the first and second target documents;
   generating the sub-corpus of documents from the corpus by computing a similarity measure between the aggregate vector representation of the first and second target documents and vector representations of each other document in the plurality of documents in the corpus;
   identifying a first plurality of concepts present in the sub-corpus;
   generating an overall importance score for a first concept of the first plurality of concepts indicating how important the first concept is with respect to the generated sub-corpus, by:
      identifying a first importance score of the first concept with respect to a first document in the sub-corpus;
      identifying a second importance score of the first concept with respect to a second document in the sub-corpus; and
      generating the overall importance score by averaging the first and second importance scores; and
   providing an indication of the generated overall importance score.

2. The method of claim 1, the method further comprising:
   generating a respective overall importance score for each respective concept of the first plurality of concepts, with respect to the generated sub-corpus, by, for each respective concept of the first plurality of concepts:
      identifying a respective importance score of the respective concept in at least two documents in the sub-corpus; and
      aggregating the respective importance scores; and
   sorting the first plurality of concepts based on the generated overall importance scores.

3. The method of claim 1, the method further comprising:
   receiving a selection of a second concept of the first plurality of concepts; and
   identifying a first subset of the sub-corpus by, for at least one respective document in the sub-corpus:
      identifying an importance score of the second concept in the respective document; and determining whether the importance score of the second concept in the respective document exceeds a first predefined threshold.

4. The method of claim 3, the method further comprising:
generating a respective overall importance score for each respective concept of a second plurality of concepts, with respect to the first subset, by, for each respective concept of the second plurality of concepts:
identifying a respective importance score of the respective concept in at least two documents in the first subset; and
aggregating the respective importance scores; and
sorting the second plurality of concepts based on the generated overall importance scores.

5. The method of claim 3, the method further comprising:
receiving a selection of a third concept of the first plurality of concepts;
identifying a second subset of the sub-corpus by, for at least one respective document in the sub-corpus:
identifying an importance score of the third concept in the respective document; and
determining whether the importance score of the third concept in the respective document exceeds a second predefined threshold.

6. The method of claim 1, wherein generating the overall importance score of the first concept with respect to the generated sub-corpus comprises assigning weights to the first and second importance scores based on the similarity measures of the aggregate vector representation.

7. The method of claim 1, the method further comprising:
receiving a selection of a third target document in the sub-corpus;
generating an aggregate vector representation of the first target document, the second target document, and the third target document; and
generating a second sub-corpus of documents in the corpus by computing a similarity measure between the aggregate vector representation of the first, second, and third documents and the vector representation of at least one other document in the plurality of documents in the corpus.

8. The method of claim 1, wherein the second target document is selected as a negative example, and wherein generating the aggregate vector representation comprises:
negating the vector representation of the second target document; and
averaging the vector representation of the first target document with the negated vector representation of the second target document.

9. A computer program product comprising:
a computer-readable storage medium having computer-readable program code embodied therewith, the computer-readable program code executable by one or more computer processors to perform an operation comprising:
generating a plurality of vector representations by processing a plurality of documents in a corpus using a passage encoder, wherein the plurality of vector representations correspond to respective documents of the plurality of documents;
identifying one or more concepts in the plurality of documents by processing the plurality of documents with the passage encoder, wherein the one or more concepts are assigned respective importance scores by the passage encoder;
receiving a selection of a first target document and a second target document from the plurality of documents to be used to generate a sub-corpus of documents from the corpus;
generating an aggregate vector representation for the first and second target documents by averaging vector representations for the first and second target documents;
generating the sub-corpus of documents from the corpus by computing a similarity measure between the aggregate vector representation of the first and second target documents and vector representations of each other document in the plurality of documents in the corpus;
identifying a first plurality of concepts present in the sub-corpus;
generating an overall importance score for a first concept of the first plurality of concepts indicating how important the first concept is with respect to the generated sub-corpus, by:
identifying a first importance score of the first concept with respect to a first document in the sub-corpus; and
identifying a second importance score of the first concept with respect to a second document in the sub-corpus; and
generating the overall importance score by averaging the first and second importance scores; and
providing an indication of the generated overall importance score.

10. The computer program product of claim 9, the operation further comprising:
generating a respective overall importance score for each respective concept of the first plurality of concepts, with respect to the generated sub-corpus, by, for each respective concept of the first plurality of concepts:
identifying a respective importance score of the respective concept in at least two documents in the sub-corpus; and
aggregating the respective importance scores; and
sorting the first plurality of concepts based on the generated overall importance scores.

11. The computer program product of claim 9, the operation further comprising:
receiving a selection of a second concept of the first plurality of concepts; and
identifying a first subset of the sub-corpus by, for at least one respective document in the sub-corpus:
identifying an importance score of the second concept in the respective document; and
determining whether the importance score of the second concept in the respective document exceeds a first predefined threshold.

12. The computer program product of claim 11, the operation further comprising:
generating a respective overall importance score for each respective concept of a second plurality of concepts, with respect to the first subset, by, for each respective concept of the second plurality of concepts:
identifying a respective importance score of the respective concept in at least two documents in the first subset; and
aggregating the respective importance scores; and
sorting the second plurality of concepts based on the generated overall importance scores.

13. The computer program product of claim 11, the operation further comprising:

receiving a selection of a third concept of the first plurality of concepts;
identifying a second subset of the sub-corpus by, for at least one respective document in the sub-corpus:
identifying an importance score of the third concept in the respective document; and
determining whether the importance score of the third concept in the respective document exceeds a second predefined threshold.

14. The computer program product of claim 9, wherein generating the overall importance score of the first concept with respect to the generated sub-corpus comprises assigning weights to the first and second importance scores based on the similarity measures of the aggregate vector representation.

15. A system comprising:
one or more computer processors; and
a memory containing a program which when executed by the one or more computer processors performs an operation, the operation comprising:
generating a plurality of vector representations by processing a plurality of documents in a corpus using a passage encoder, wherein the plurality of vector representations correspond to respective documents of the plurality of documents;
identifying one or more concepts in the plurality of documents by processing the plurality of documents with the passage encoder, wherein the one or more concepts are assigned respective importance scores by the passage encoder;
receiving a selection of a first target document and a second target document from the plurality of documents to be used to generate a sub-corpus of documents from the corpus;
generating an aggregate vector representation for the first and second target documents by averaging vector representations for the first and second target documents;
generating the sub-corpus of documents from the corpus by computing a similarity measure between the aggregate vector representation of the first and second target documents and vector representations of each other document in the plurality of documents in the corpus;
identifying a first plurality of concepts present in the sub-corpus;
generating an overall importance score for a first concept of the first plurality of concepts indicating how important the first concept is with respect to the generated sub-corpus, by:
identifying a first importance score of the first concept with respect to a first document in the sub-corpus; and
identifying a second importance score of the first concept with respect to a second document in the sub-corpus; and
generating the overall importance score by averaging the first and second importance scores; and
providing an indication of the generated overall importance score.

16. The system of claim 15, the operation further comprising:
generating a respective overall importance score for each respective concept of the first plurality of concepts, with respect to the generated sub-corpus, by, for each respective concept of the first plurality of concepts:
identifying a respective importance score of the respective concept in at least two documents in the sub-corpus; and
aggregating the respective importance scores; and
sorting the first plurality of concepts based on the generated overall importance scores.

17. The system of claim 15, the operation further comprising:
receiving a selection of a second concept of the first plurality of concepts; and
identifying a first subset of the sub-corpus by, for at least one respective document in the sub-corpus:
identifying an importance score of the second concept in the respective document; and
determining whether the importance score of the second concept in the respective document exceeds a first predefined threshold.

18. The system of claim 17, the operation further comprising:
generating a respective overall importance score for each respective concept of a second plurality of concepts, with respect to the first subset, by, for each respective concept of the second plurality of concepts:
identifying a respective importance score of the respective concept in at least two documents in the first subset; and
aggregating the respective importance scores; and
sorting the second plurality of concepts based on the generated overall importance scores.

19. The system of claim 17, the operation further comprising:
receiving a selection of a third concept of the first plurality of concepts;
identifying a second subset of the sub-corpus by, for at least one respective document in the sub-corpus:
identifying an importance score of the third concept in the respective document; and
determining whether the importance score of the third concept in the respective document exceeds a second predefined threshold.

* * * * *